United States Patent [19]
Frese et al.

[11] Patent Number: 4,486,711
[45] Date of Patent: Dec. 4, 1984

[54] GRADIENT FIELD COIL SYSTEM FOR NUCLEAR SPIN TOMOGRAPHY

[75] Inventors: Georg Frese; Horst Siebold, both of Erlangen, Fed. Rep. of Germany

[73] Assignee: Siemens Aktiengesellschaft, Munich, Fed. Rep. of Germany

[21] Appl. No.: 406,454

[22] Filed: Aug. 9, 1982

[30] Foreign Application Priority Data

Aug. 27, 1981 [DE] Fed. Rep. of Germany ....... 3133873

[51] Int. Cl.$^3$ ............................................. G01R 33/08
[52] U.S. Cl. ...................................... 324/319; 324/320
[58] Field of Search .......................... 324/300, 318–320

[56] References Cited

U.S. PATENT DOCUMENTS

| | | | |
|---|---|---|---|
| 3,569,823 | 3/1971 | Golay | 324/320 |
| 4,339,718 | 7/1982 | Bull | 324/320 |
| 4,398,149 | 8/1983 | Zens | 324/319 |

*Primary Examiner*—Michael J. Tokar
*Attorney, Agent, or Firm*—Kenyon & Kenyon

[57] ABSTRACT

A gradient coil system for an image-generating, nuclear magnetic resonance tomographic apparatus, particularly a zeugmatographic apparatus. The gradient coil system is arranged on a hollow cylindrical support body having an axis which extends along the z-direction of an x, y, z coordinate system which has an origin in the center of an imaging region. The gradient coil system contains, in addition to ring-shaped individual coils for generating field gradients which are substantially constant in the imaging region, a plurality of saddle-shaped coils which are symmetrically arranged through the imaging center for generating field gradients in the x and y directions. The saddle-shaped coils have straight conductor sections extending in the z-direction and arc-shaped conductor sections which extend perpendicularly with respect to the z-axis and along the circumferential direction of the support body. In accordance with the invention, a further arc-shaped conductor section is connected in parallel with the arc-shaped conductor sections, the further arc-shaped conductor section facing a plane of symmetry. All of the arc-shaped conductor sections are displaced in the z-direction from the plane of symmetry by predetermined distances, and each arc-shaped conductor section has an electric linkage factor which is responsive to the distance between the particular arc-shaped conductor section and the plane of symmetry.

22 Claims, 2 Drawing Figures

GRADIENT FIELD COIL SYSTEM FOR NUCLEAR SPIN TOMOGRAPHY

BACKGROUND OF THE INVENTION

This invention relates generally to gradient field coil systems for image-generating apparatus which is used in nuclear magnetic resonance tomography, and more particularly, to an arrangement where a gradient coil system is arranged on at least one hollow cylindrical support body wherein a magnetic field has a field gradient which is essentially constant in the imaging region.

In image-generating apparatus for nuclear magnetic resonance technology, particularly for zeugmatography, a gradient coil field system is arranged on at least one hollow cylindrical support body having a radius r; the cylinder having an axis which extends in the z-direction of an orthogonal x, y, and z coordinate system with the coordinate origin in the center of the imaging region. In this system, a base field magnet is oriented to produce a magnetic field $B_z$ in the z-direction. Magnetic field $B_z$ is formed by at least two ring-shaped individual coils which are arranged approximately symmetrically with respect to the x-y plane through the center of the imaging region to produce a field gradient $G_z = \delta B_z/\delta z$. Current flows in opposite directions through the two ring-shaped coils. The coil system further contains at least one set of a pair of saddle-shaped individual coils which are arranged at least approximately symmetrically with respect to the plane of symmetry, and which are provided for generating field gradients $G_x = \delta B_z/\delta x$ in the x-direction and $G_y = \delta B_z/\delta y$ in the y-direction. Each of these saddle-shaped individual coils has straight conductor sections extending in the z-direction and arc-shaped conductor sections extending in the circumferential direction of the carrier body perpendicular to the z-axis. Current is conducted through the respective pairs of coils for each of the x and y directions such that the current flow directions are the same in adjacent straight conductor sections of the individual coils of each coil pair, but are opposed in the straight conductor sections of the coils which are arranged symmetrically with respect to the plane of symmetry. Such a gradient coil system is known from U.S. Pat. No. 3,569,823.

In the field of medical diagnostics, imaging methods have been proposed wherein an image similar to an X-ray tomogram is constructed by numerical or measurement analysis of integrated proton resonance signals from the spatial spin density and/or relaxation time distribution of a human body to be examined. The corresponding method is also known as "zeugmatography" or nuclear spin tomography. See: "Nature", volume 242, 1973, pages 190 to 191.

According to the known methods of nuclear spin tomography three different kinds of coil systems are required, in principle. One magnet is required to generate a stationary base field $B_z$ which must be as homogeneous as possible and having an order of magnitude of between 0.05 to 0.5 Tesla. Magnetic field $B_z$ is assumed to be oriented, for example, in the z-direction of an orthogonal x, y, z coordinate system. Moreover, the z-direction is the examination axis along which a body, particularly a human body to be examined, is placed in the magnetic field. The coordinate origin is to be situated in the imaging, or examination region. Furthermore, a high-frequency coil arrangement is to be provided for the corresponding precession frequency of the nuclear spin to be considered, in order to excite the nuclear spin, and optionally, to receive the induction signals. If the high-frequency coil arrangement is used for detecting these signals, a separate receiving coil system may also be provided. Finally, a system of gradient coils is needed which generate a preferably orthogonal set of supplementary fields $G_z = \delta B_z/\delta z$; $G_x = \delta B_z/\delta x$; and $G_y = \delta B_z/\delta y$. These supplementary fields are small in comparison with the base field $B_z$ which is oriented in the z-direction. Only the gradient fields which are switched on in the predetermined sequence permit a distinction in the location due to the shape of the precession frequency of the nuclei. See, for example, "Journal of Magnetic Resonance", volume 18, 1975, pages 69 to 83; volume 29, 1978, pages 355 to 373.

If the gradients $G_x$, $G_y$, and $G_z$ in an imaging region are not constant to a high degree, but are still functions of the location itself, blurred, distorted, and artifical images are generated. Linearity of the gradient fields and the constancy of their derivatives $G_x$, $G_y$, and $G_z$ in the imaging region are therefore an essential condition for high image quality of nuclear spin tomographic apparatus.

Generally, the three gradients can be generated by magnetic quadrupoles. The fact that the coils for generating the gradients must be arranged inside the base field magnet must be taken into consideration in the design of nuclear magnetic resonance apparatus. Thus, sufficient space must be left for placing the human body to be examined.

An analytic derivation of the geometry of such coil systems can be obtained from the above-mentioned U.S. Pat. No. 3,569,823. Thus, the coils in the coil system are to produce a magnetic field which is developed into spherical functions which are as pure as possible. It is assumed here that the field-generating conductors are arranged on the outside and/or inside cylindrical surfaces of a hollow cylindrical support body. In such an arrangement, disturbances of the main spherical functions which are generated by the finite length of the conductors and their locations are analytically minimized.

The hollow cylindrical support body with the corresponding gradient coils can be inserted into a field magnet having an axis which coincides with the axis of the base magnet and which points, for example, in the z-direction of an orthogonal x, y, z coordinate system. The z-gradient $G_z$ is generated by two ring coils through which current flows in opposite directions. In order to generate the x-gradient $G_x$ two saddle-shaped coil pairs are placed on the support body. For the y-gradient $G_y$, a corresponding system of four saddle-shaped coils is provided which are arranged opposite to the x-gradient coils either on the outer or inner cylindrical surfaces of the cylindrical support body, shifted by 90° in the circumferential direction. The two pairs of individual coils of each coil set are arranged symmetrically with respect to an x-y plane which is oriented perpendicularly to the cylinder axis and extends through the center of the imaging region.

In the calculation of this coil system it is stipulated that high linearity of the gradient field in the radial x-y plane is achieved. The x-y plane also represents the plane of symmetry through the imaging region. In order to take pictures of the entire body using nuclear magnetic resonance tomographic apparatus, linearity in this field is required not only in a two dimensional plane imaging region, but in a spherical volume having a radius of, for example, 20 cm because it is desirable to orient the imaging plane in space in any manner desired. This, however, requires that the gradient field be linear over the entire volume. The gradients are to be constant down to less than 5% in order to prevent substantial distortion of the image.

It is, therefore, an object of the present invention to develop a gradient coil system wherein a dimensionally extending imaging region having high linearity of the x and/or y gradients is obtained in a relatively simple and inexpensive manner.

SUMMARY OF THE INVENTION

The foregoing and other objects are achieved by this invention which provides a further arc-shaped conductor section connected in parallel with the arc-shaped conductor sections of the saddle-shaped individual coils which face the plane of symmetry for generating the field gradients $G_x$ and $G_y$. The arc-shaped conductor sections of the individual coils are arranged at predetermined distances from the plane of symmetry. Moreover, the arc-shaped conductor sections are electrically linked with one another, such electrical linkages having predetermined values which increase with increasing distances from the plane of symmetry.

The advantages which are associated with this embodiment of the gradient coil system include a pronouned linearity region in the z-direction which is achieved by splitting, in accordance with the invention, the arc-shaped conductor section facing the plane of symmetry into two conductor arcs, respectively. In addition, the linearity region is improved by the predetermined electric linkage through the conductor arcs. This can be achieved while the dimensions of the individual coils can be kept small so as to limit the current comsumption and the inductance of the coils. The gradient fields can then be switched on and off in short times, as is required for many image-generating devices.

BRIEF DESCRIPTION OF THE DRAWINGS

Comprehension of the invention is facilitated by reading the following detailed description in conjunction with the annexed drawings, in which.

DETAILED DESCRIPTION

Figure 1:
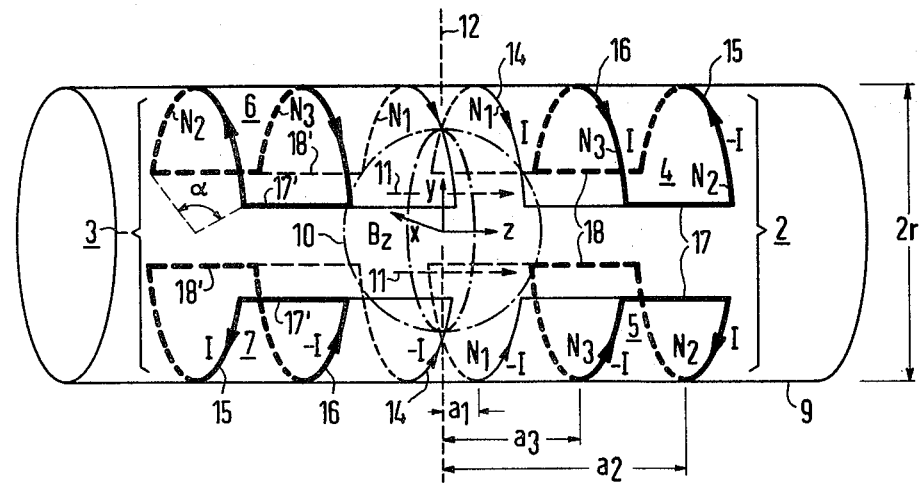
FIG. 1 is a schematic representation of the x or y gradient coils of an image-generating apparatus which utilizes nuclear spin resonance technology.

In known apparatus for the practice of nuclear magnetic resonance technology, illustratively nuclear spin tomography or zeugmatography, a known magnet coil system, such as is described in U.S. Pat. No. 3,569,823, is used to provide a base magnetic field. The present inventive gradient coil system may be used to improve the known arrangement which comprises at least one normal conducting, or superconducting, field coil system arranged concentrically with respect to the z-axis of an orthogonal x, y, z coordinate system. The known magnet coil arrangement generates a homogeneous magnetic base field in the z-direction. Furthermore, gradient coils for generating constant magnetic field gradients in an imaging region are provided. The origin of the x, y, z coordinate system is located in the center of the imaging region. The magnet coils are arranged so that the center of the homogeneous field region is accessible along the axial direction to permit, for example, a human body to be examined to be placed in the magnetic field along the z-axis. Nuclear spin is excited by means of a high-frequency field which is directed perpendicularly to the z-axis. The high-frequency field is generated by coils which also serve as receiver coils for receiving the nuclear spin resonance signals.

As noted, the present inventive gradient coil system may be incorporated in the known nuclear magnetic resonance tomographic apparatus. The inventive coil system comprises x and y gradient coils, of which one coil system, illustratively the system for generating the y-gradient, is schematically illustrated in the oblique view of FIG. 1. Conductor portions which are not normally visible in this view are indicated in phantom by dashed lines. The coil system by which substantially linear gradient fields are to be generated in the x and y directions in an imaging region is provided with two pairs 2 and 3, each having two saddle-shaped individual coils 4, 5, and 6, 7. The individual coils are arranged on the outer and/or inner surfaces of a hollow cylindrical support body 9, the outside or inside radius of which has a magnitude r. The axis of the cylinder is oriented in the z-direction of an orthogonal x, y, z coordinate system. The z-axis is also the examination axis, along which a body to be examined can be placed in the examination, or imaging, region 10 which is indicated by dash-dotted lines. In this region, a base field magnet which is indicated by dashed arrows 11 produces a magnetic field $B_z$ which is substantially homogeneous and oriented in the z-direction. The coordinate origin of the x, y, z coordinate system is located at the center of the imaging region.

The two coil pairs 2 and 3 are arranged symmetrically with respect to an x-y plane which extends through the center of the imaging region. This plane of symmetry is indicated by a dashed line 12.

Each of the four individual coils 4 to 7 contains an arc-shaped conductor section 14 at its end face which faces plane of symmetry 12. Arc-shaped conductor section 14 is provided with a number of turns $N_1$ and an outer arc-shaped conductor section 15 which is further removed from the plane of symmetry and has a number of turns $N_2$. A further arc-shaped conductor section 16 which is connected electrically parallel with the arc-shaped conductor section 14 faces the plane of symmetry and has a number of turns $N_3$. The length of the arc-shaped conductor sections 14 to 16 in the circumferential direction is selected so that a central arc angle $\alpha$ is between 90° and 150°. In a preferred embodiment of the invention, the arc-shaped conductor section should correspond to an angle $\alpha$ of between 121° to 134°. This structure with the plural arc-shaped coil sections ensures a sufficiently high degree of linearity of the x-gradient fields for the practice of nuclear spin resonance tomography.

Arc-shaped conductor sections 14 to 16 have predetermined distances from the plane of symmetry and are assembled via straight conductor sections 17 and 18, and 17' and 18', which extend in the z-direction to form the respective saddle-shaped coils. In addition, a substantially large electric linkage is selected for arc-shaped conductor section 15 which is further removed from the plane of symmetry than arc-shaped conductor sections 14 which face the plane of symmetry. The term "electric linkage" is understood here to mean the product of the magnitude of the current I and the respective number of turns N of a coil section. This product is also called the number of ampere turns. The magnitude of the electric linkage in conductor section 16 between arc-shaped conductor sections 14 and 15 should be between the magnitudes of the linkages in the conductor sections at the end face. The electric linkages $I \times N_1$, $I \times N_3$, and $I \times N_2$ of arc-shaped conductor sections 14, 16, and 15 therefore have values which become larger with increasing distance from plane of symmetry 12.

In one embodiment, a distance $a_1$ along the z-direction between plane of symmetry 12 and arc-shaped conductor sections 14 is advantageously selected to have a value between 0.1 r and 0.4 r. In a preferred embodiment, distance $a_1$ should have a value of about 0.24 r. A distance $a_2$ between arc-shaped conductors 15 and plane of symmetry 12 has a value between $2.5a_1$ and $100a_1$, and preferably about $7a_1$ which corresponds to 1.71 r. On either side of plane of symmetry 12, conductor sections 16 are always located intermediate of respective conductor sections 15 and 14. A distance $a_3$ between plane of symmetry 12 and arc-shaped conductor sections 16 depends upon distances $a_1$ and $a_2$ and, in this embodiment, has a value between $1.25a_1$ and $0.75a_2$. Preferably, $a_3$ should have a value of about $0.5 (a_1 + a_2)$.

FIG. 1 further shows arc-shaped conductor sections 14 to 16 represented by lines of different widths. Electric linkages are provided for these conductor sections which are substantially larger in the outer arc-shaped conductor section 15 and central arc-shaped conductor section 16, than in the arc-shaped conductor section 14 which faces the plane of symmetry. Electric linkage $I \times N_2$ for arc-shaped conductor section 15 has a magnitude which is advantageously selected to be two to five times larger, and preferably about 3.25 times larger, than the magnitude of electric linkage $I \times N_1$ for arc-shaped conductor section 14. The magnitude of electric linkage $I \times N_3$ in central arc-shaped conductor section 3 is selected to be between $1.1 \times I \times N_1$ and $4.5 \times I \times N_1$, where this value is always selected to be smaller than the value of electric linkage $I \times N_2$. In one advantageous embodiment a value of the magnitude $2.25 \times I \times N_1$ is selected for the electric linkage for central arc-shaped conductor section 16.

Since the central arc-shaped conductor sections are to be connected electrically parallel with the associated conductor sections 14 which face the plane of symmetry, the current I always flows in the same direction in the conductor sections. In contrast thereto, the flow of current in outer arc-shaped conductor section 15 is opposed thereto.

As is further shown in FIG. 1 by the arrow heads at the individual conductor sections, currents flow through individual coils 4 to 7 in such a manner that current flows in the same direction along adjacent conductor sections 17 or 18, and 17' or 18' of individual coils 4 and 5, or 6 and 7 of each coil pair 2 or 3. Furthermore, the current flow directions in these straight conductor sections 17 and 18 are opposed in one coil pair 2 to the current flow directions in the corresponding conductor sections 17' and 18' of the other coil pair 3. Thus, current flows through both straight conductor sections 17 in the same direction with respect to the z-axis. This direction is the same as the current flow direction in straight conductor section 18', but opposite to the flow directions in straight conductor sections 17' and 18. In this manner, not only are the individual coils 4, 6 and 5, 7 arranged symmetrically to each other with respect to plane of symmetry 12, but the current flow directions are likewise symmetrical with respect to this symmetry plane.

With this choice of current flow directions, and assuming the above distances $a_1$ to $a_3$ correspond with electric linkages $I \times N_1$ to $I \times N_3$, as above, an imaging region 10 is advantageously created which has substantially constant field gradients $G_x$ and $G_y$ in an approximately spherical volume having a radius of about $(\frac{2}{3})r$. It does not matter here whether, as assumed in the embodiment of FIG. 1, the magnitude of the current through the arc-shaped conductor sections is the same and only their number of turns is different, or whether also different currents are provided in order to obtain the mentioned values of the electric linkages in these arc-shaped conductor sections.

Figure 2:
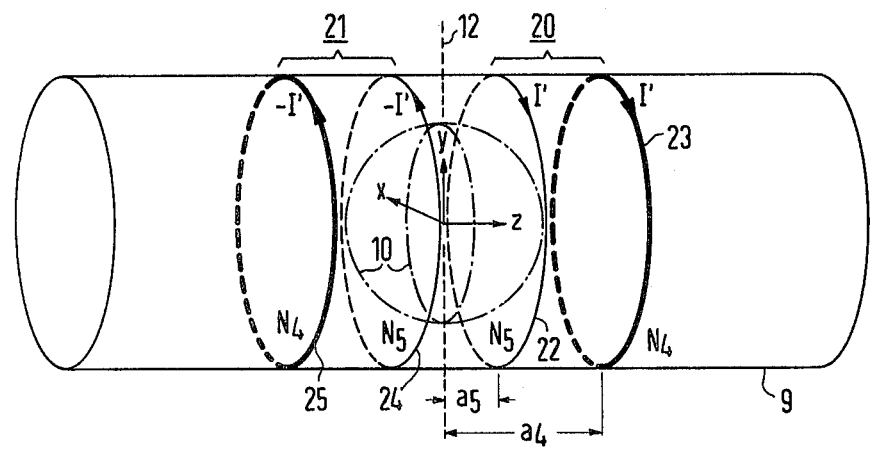
FIG. 2 is a schematic representation of the z-gradient coils of the apparatus.

The gradient coils, not shown in FIG. 1, for generating sufficiently linear field gradients $G_z$ in the z-direction may be corresponding coils of known apparatus such as is described in U.S. Pat. No. 3,569,823, DE OS No. 28 40 178, or the published European patent application EP No. 21 535 A1. FIG. 2 shows an oblique schematic representation of special z gradient coils which are designed in accordance with the invention. The z-gradient coil system comprises two pairs 20 and 21, each with two ring-shaped individual coils 22, 23, and 24, 25, respectively. These individual coils are arranged on the inner and outer surfaces of hollow cylindrical support body 9 which is provided for the coil system according to the invention, as shown in FIG. 1. As noted above, hollow cylindrical support body 9 has a diameter having a magnitude 2r. Elements of structure in FIG. 2 which correspond to the elements described in FIG. 1 are similarly designated.

In order to ensure sufficient linearity of the z-gradient fields, individual coils 22 to 25 are arranged at predetermined distances from the plane of symmetry through the coordinate system. In addition, a substantially larger electric linkage is chosen for the individual coils 23 and 25 which are further away from plane of symmetry 12, than for individual coils 22 and 24 which face the plane of symmetry. A distance $a_4$ between outer individual coils 23 and 25 from plane of symmetry 12 has a value which is advantageously selected to be between 0.9 r and 1.3 r. In a preferred embodiment, a value of 1.1 r is selected. A distance $a_5$ of individual coils 22 and 24 which face plane of symmetry 12 depends upon the distance $a_4$ and is advantageously selected to be between $0.25a_4$ and $0.5a_4$. A preferred value is approximately $0.33a_4$.

A current having a magnitude I' flows through individual turns $N_4$ and $N_5$ of coils 23, 25 and 22, 24, respectively. A ratio of the electric linkage $I' \times N_4$ of outer individual coils 23 and 25 to electric linkage $I' \times N_5$ of individual coils 22 and 24, which are arranged at distances $a_4$ and $a_5$, respectively, is selected to be between 6:1 and 12:1. In a particularly advantageous embodiment, this ratio is approximately 9:1.

For the mentioned values of distances $a_4$ and $a_5$, and linkages $I' \times N_4$ and $I' \times N_5$, an imaging region 10 is achieved having a largely constant field gradient $G_z$ which has an approximately spherical shape with radius of approximately $(\frac{2}{3})r$.

With respect to the embodiment of FIG. 2, it was assumed that the magnitude of the current through the four individual coils 22 to 25 is the same and only the number of turns $N_4$ and $N_5$ is different. However, it is equally possible to adjust the currents in coils 22, 24 and 23, 25 differently so as to obtain the predetermined values for the electric linkage through these coils.

Although the invention has been described in terms of specific embodiments and applications, persons skilled in the art, in light of this teaching, can generate additional embodiments without exceeding the scope or departing from the spirit of the claimed invention. Accordingly, it is to be understood that the drawings and descriptions in this disclosure are proffered to facilitate comprehension of the invention and should not be construed to limit the scope thereof.

What is claimed is:

1. A gradient coil system for an image-generating, nuclear magnetic resonance tomographic apparatus, the gradient coil system being arranged on at least one hollow cylindrical carrier, the cylindrical carrier having a radius r and a central axis which extends along the z-direction of an orthogonal x, y, z coordinate system, the coordinate system having an origin located in the center of an imaging region within said carrier, the system having a base field magnet for producing a magnetic field $B_z$ in the z-direction, the magnetic field of said gradient coil system having a field gradient $G_z = \delta B_z / \delta z$ which is essentially constant in the imaging region, the system further having at least two ring-shaped coils arranged symmetrically with respect to an x-y plane of symmetry through the center of the imaging region for conducting current in opposite directions, at least two pairs of saddle-shaped coils arranged approximately symmetrically with respect to the plane of symmetry for generating a field gradient $G_x = \delta B_z / \delta x$ in the x-direction and a corresponding field gradient $G_y = \delta B_z / \delta y$ in the y-direction, the field gradients being substantially constant, the saddle-shaped coils being coupled to a source of electrical current and each having respective straight conductor sections in the z-direction and first and second arc-shaped conductor sections in the circumferential direction perpendicular to the z-axis, said first arc-shaped conductor section being arranged adjacent said plane of symmetry and said second arc-shaped conductor section being arranged farther away from said plane of symmetry than said first arc-shaped conductor section, adjacent straight conductor sections in each pair of the saddle-shaped coils conducting electrical current in the same direction with respect to each other, and in the opposite direction with respect to corresponding straight conductor sections in the other pair of saddle-shaped coils arranged symmetrically on the other side of the plane of symmetry, the gradient coil system further comprising a third arc-shaped conductor section in each saddle-shaped coil, said third arc-shaped conductor section being connected in parallel with the first arc-shaped conductor section of the associated saddle-shaped coil, said third arc-shaped conductor section being arranged between the first and second arc-shaped conductor sections, the first, second and said third arc-shaped conductor sections being arranged at respective first, second, and third predetermined distances from the plane of symmetry and each containing a respective number of turns of conductive material, the first, second and said third arc-shaped conductor sections having respective predetermined electric linkage factors, magnitudes of said electric linkage factors being equal to a product of the electrical current being conducted through the respective arc-shaped conductor section and the number of turns of conductive material in the respective arc-shaped conductor section, the magnitudes of said electric linkage factors corresponding to said respective distances of the first, second, and said third arc-shaped conductor sections from the plane of symmetry.

2. The gradient coil system of claim 1 wherein said first predetermined distance between said first arc-shaped conductor section and the plane of symmetry is between 0.1 r and 0.4 r.

3. The gradient coil system of claim 2 wherein said first predetermined distance is approximately 0.24 r.

4. The gradient coil system of claim 1 wherein the second arc-shaped conductor section is located at said second predetermined distance from the plane of symmetry, said second predetermined distance being greater than said first and third predetermined distances, said second predetermined distance being between 2.5 and 100 times greater than said first predetermined distance.

5. The gradient coil system of claim 4 wherein said second predetermined distance which corresponds to the distance between the plane of symmetry and the second arc-shaped conductor section, said second predetermined distance being approximately 7 times greater than said first predetermined distance which corresponds to the distance between the plane of symmetry and said first arc-shaped conductor section.

6. The gradient coil system of claim 4 or 5 wherein said second predetermined distance has a value of approximately 1.71 r.

7. The gradient coil system of claim 1 wherein said third predetermined distance which corresponds to the distance between the plane of symmetry and the third arc-shaped conductor section is between 1.25 times the distance of said first arc-shaped conductor section from the plane of symmetry, and 0.75 times the distance of the second arc-shaped conductor section from the plane of symmetry, the second arc-shaped conductor section being furthest from the plane of symmetry.

8. The gradient coil system of claim 7 wherein said third predetermined distance has a value which corresponds to approximately one-half of the sum of said first and second predetermined distances.

9. The gradient coil system of claim 1 wherein said electric linkage factor of the second arc-shaped conductor section is between two and five times greater than said electric linkage factor of said first arc-shaped conductor section, said second predetermined distance between the second arc-shaped conductor section and the plane of symmetry being greater than said first and third predetermined distances.

10. The gradient coil system of claim 9 wherein said electric linkage factor of the second arc-shaped conductor section is approximately 3.25 times greater than said electric linkage factor of said first arc-shaped conductor section.

11. The gradient coil system of claim 1 wherein said electric linkage factor of the third arc-shaped conductor section is between 1.1 and 4.5 times greater than said electric linkage factor of said first arc-shaped conductor section, said electric linkage factor of the third arc-shaped conductor section always being smaller than said electric linkage factor of the second arc-shaped conductor section.

12. The gradient coil system of claim 11 wherein said electric linkage factor of the third arc-shaped section is approximately 2.25 times greater than said electric linkage factor of said first arc-shaped conductor section.

13. The gradient coil system of claim 9 wherein at least one of the first, second, and said third arc-shaped conductor sections conducts a current having a different value from the other arc-shaped conductor sections.

14. The gradient coil system of claim 1 wherein there are further provided two pairs of first and second ring-shaped coils, said pairs being arranged approximately symmetrically with respect to the plane of symmetry, said ring-shaped coils of one of said pairs conducting current in a direction opposite to the direction of the current in said ring-shaped coils of the other pair, the ring-shaped coils of each pair being arranged at respective first and second predetermined distances from the plane of symmetry, said first and second ring-shaped coils of each pair having respective electric linkage factors wherein said first ring-shaped coil, which is further from the plane of symmetry than said second ring-shaped coil, has an electric linkage factor which is substantially larger than the electric linkage factor of the second ring-shaped coil.

15. The gradient coil system of claim 14 wherein said predetermined distance of said first ring-shaped coil is between 0.9 r and 1.3 r.

16. The gradient coil system of claim 15 wherein said predetermined distance of said first ring-shaped coil is approximately 1.1 r.

17. The gradient coil system of claim 14, 15, or 16 wherein said predetermined distance between said second ring-shaped coil and the plane of symmetry is between 0.25 and 0.5 times the predetermined distance of said first ring-shaped coil.

18. The gradient coil system of claim 17 wherein said predetermined distance of said second ring-shaped coil is approximately 0.33 times the distance of said first ring-shaped coil.

19. The gradient coil system of claim 14 wherein said electric linkage factor of said first ring-shaped coil is between six and twelve times greater than said electric linkage factor of said second ring-shaped coil.

20. The gradient coil system of claim 19 wherein said electric linkage factor of said first ring-shaped coil is approximately nine times greater than the electric linkage factor of said second ring-shaped coil.

21. The gradient coil system of claim 1 wherein the first, second, and said third arc-shaped conductor sections extend for respective predetermined distances along the circumference of the cylindrical carrier so as to define respective aperture angles with respect to the central axis, said aperture angles having values between 90° and 150°.

22. The gradient coil system of claim 21 wherein said aperture angles are between 121° and 134°.

* * * * *